US 009470704 B2

(12) United States Patent
Nadkarni et al.

(10) Patent No.: US 9,470,704 B2
(45) Date of Patent: Oct. 18, 2016

(54) WEARABLE MOTION SENSING DEVICE (71) Applicant: Nortek Security & Control LLC, Carlsbad, CA (US)

(72) Inventors: Vijay Nadkarni, San Jose, CA (US); Jeetendra Jangle, Fremont, CA (US)

(73) Assignee: Nortek Security & Control LLC, Carlsbad, CA (US)

( * ) Notice: Subject to any disclaimer, the term of this patent is extended or adjusted under 35 U.S.C. 154(b) by 403 days.

(21) Appl. No.: 13/975,294

(22) Filed: Aug. 24, 2013

(65) Prior Publication Data

US 2013/0345578 A1  Dec. 26, 2013

Related U.S. Application Data

(63) Continuation-in-part of application No. 12/891,108, filed on Sep. 27, 2010, now Pat. No. 8,972,197, which is a continuation-in-part of application No. 12/560,069, filed on Sep. 15, 2009, now abandoned.

(60) Provisional application No. 61/208,344, filed on Feb. 23, 2009.

(51) Int. Cl.
| | | |
|---|---|---|
| *G01P 15/00* | (2006.01) |
| *G01P 1/12* | (2006.01) |
| *A61B 5/0408* | (2006.01) |
| *G06K 9/00* | (2006.01) |
| *G06F 19/00* | (2011.01) |
| *A61B 5/00* | (2006.01) |
| *A61B 5/0205* | (2006.01) |
| *A61B 5/0402* | (2006.01) |

(52) U.S. Cl.
CPC .............. *G01P 1/12* (2013.01); *A61B 5/0408* (2013.01); *A61B 5/6802* (2013.01); *A61B 5/6822* (2013.01); *A61B 5/7246* (2013.01); *G06F 19/3418* (2013.01); *G06F 19/3481* (2013.01); *G06K 9/00342* (2013.01); *A61B 5/0205* (2013.01); *A61B 5/0402* (2013.01); *A61B 5/726* (2013.01); *A61B 2562/0219* (2013.01)

(58) Field of Classification Search
CPC .................................. G06F 3/014; G08B 1/00
See application file for complete search history.

(56) References Cited

U.S. PATENT DOCUMENTS

| | | | |
|---|---|---|---|
| 4,513,437 | A | 4/1985 | Chainer et al. |
| 6,028,626 | A | 2/2000 | Aviv |
| 6,265,982 | B1 | 7/2001 | Ostwald |
| 6,626,728 | B2 | 9/2003 | Holt |
| 6,675,649 | B2 | 1/2004 | Uchiyama et al. |
| 6,756,889 | B2 | 6/2004 | Sala et al. |

(Continued)

OTHER PUBLICATIONS

Response to Office Action submitted Jan. 23, 2011, for U.S. Appl. No. 12/560,069, filed Sep. 15, 2009.

(Continued)

*Primary Examiner* — Elias Desta
(74) *Attorney, Agent, or Firm* — Schwegman Lundberg & Woessner, P.A.

(57) ABSTRACT

A wearable motion sensing device is disclosed. One embodiment of the wearable motion sensing device includes a motion sensor, and a pendant that is attached to the wearable motion sensing device, wherein the pendant is attached to the wearable motion sensing device at a location of the wearable motion sensor relative to the motion sensor that when worn by a human being, a mass of the pendant urges the motion sensor towards the human being.

12 Claims, 7 Drawing Sheets

(56) References Cited

U.S. PATENT DOCUMENTS

| | | |
|---|---|---|
| 6,802,814 B2 | 10/2004 | Narimatsu |
| 6,816,766 B2 | 11/2004 | Sala et al. |
| 6,999,863 B2 | 2/2006 | Neal et al. |
| 7,071,828 B2 * | 7/2006 | Wong .................. G08B 5/38 340/573.1 |
| 7,145,461 B2 | 12/2006 | Lehrman et al. |
| 7,248,172 B2 | 7/2007 | Clifford et al. |
| 7,467,060 B2 | 12/2008 | Kulach et al. |
| 7,715,982 B2 | 5/2010 | Grenfell et al. |
| 7,827,000 B2 | 11/2010 | Stirling et al. |
| 8,060,337 B2 | 11/2011 | Kulach et al. |
| 8,972,197 B2 | 3/2015 | Jangle et al. |
| 2003/0158489 A1 | 8/2003 | Narimatsu |
| 2005/0154512 A1 | 7/2005 | Schubert et al. |
| 2006/0005578 A1 | 1/2006 | Tortoli |
| 2006/0089538 A1 | 4/2006 | Cuddihy et al. |
| 2006/0282021 A1 | 12/2006 | DeVaulet et al. |
| 2007/0167693 A1 | 7/2007 | Scholler et al. |
| 2007/0293781 A1 | 12/2007 | Sims et al. |
| 2008/0001735 A1 * | 1/2008 | Tran .................. G06F 19/3418 340/539.22 |
| 2008/0256796 A1 | 10/2008 | Fix |
| 2009/0303204 A1 | 12/2009 | Nasiri et al. |
| 2010/0073284 A1 | 3/2010 | Dods et al. |
| 2010/0121226 A1 | 5/2010 | Ten Kate et al. |
| 2010/0217533 A1 | 8/2010 | Nadkarni et al. |

OTHER PUBLICATIONS

Response to Office Action submitted Apr. 2, 2013, for U.S. Appl. No. 12/621,099, filed Nov. 18, 2009.
Response to Office Action submitted May 10, 2012, for U.S. Appl. No. 12/883,304, filed Sep. 16, 2010.

* cited by examiner

WEARABLE MOTION SENSING DEVICE

RELATED APPLICATIONS

This patent application claim is a continuation-in-part (CIP) of U.S. patent application Ser. No. 12/891,108, filed Sep. 27, 2010, is a continuation-in-part (CIP) of U.S. patent application Ser. No. 12/560,069, filed on Sep. 15, 2009, which claims priority to US provisional patent application Ser. No. 61/208,344 filed on Feb. 23, 2009, which are all incorporated by reference.

FIELD OF THE DESCRIBED EMBODIMENTS

The described embodiments relate generally to motion detecting. More particularly, the described embodiments relate to a wearable motion sensing device.

BACKGROUND

There is an increasing need for remote monitoring of individuals, animals and inanimate objects in their daily or natural habitats. Many seniors live independently and need to have their safety and wellness tracked. A large percentage of society is fitness conscious, and desire to have, for example, workouts and exercise regimen assessed. Public safety officers, such as police and firemen, encounter hazardous situations on a frequent basis, and need their movements, activities and location to be mapped out precisely.

The value in such knowledge is enormous. Physicians, for example, like to know their patients sleeping patterns so they can treat sleep disorders. A senior living independently wants peace of mind that if he has a fall it will be detected automatically and help summoned immediately. A fitness enthusiast wants to track her daily workout routine, capturing the various types of exercises, intensity, duration and caloric burn. A caregiver wants to know that her father is living an active, healthy lifestyle and taking his daily walks. The police would like to know instantly when someone has been involved in a car collision, and whether the victims are moving or not.

It is desirable to have an apparatus and method that can accurately monitor the motion of, for example, a human being.

SUMMARY

A first embodiment includes wearable motion sensing device. The wearable motion sensing device includes a motion sensor, and a pendant that is attached to the wearable motion sensing device, wherein the pendant is attached to the wearable motion sensing device at a location of the wearable motion sensing device relative to the motion sensor that when worn by a human being, a mass of the pendant urges the motion sensor towards the human being.

A second embodiment includes a wearable motion sensing device. The wearable motion sensing device includes a motion sensor attached to the wearable motion sensing device at a first location, and a pendant attached to the wearable motion sensing device at a second location. Further, the pendant includes a processor for processing electronic signals received from the motion sensor, and a power supply.

A third embodiment includes a method of detecting motion of a human. The method includes placing a wearable motion sensing device on the human, wherein the wearable motion sensing device includes a pendant that is attached to the wearable motion sensing device at a location of the wearable motion sensing device relative to a motion sensor of the wearable motion sensing device wherein a mass of the pendant urges the motion sensor towards the human being. The method further includes generating an acceleration signature based on sensed acceleration of the motion sensor.

Other aspects and advantages of the described embodiments will become apparent from the following detailed description, taken in conjunction with the accompanying drawings, illustrating by way of example the principles of the described embodiments.

DETAILED DESCRIPTION

The described embodiments include wearable motion sensing devices. Various embodiments of these devices, carried or worn by people on their bodies, have the ability to detect changes in acceleration, spatial orientation, gravitational force and angular momentum, and thereby provide a measure of the types of motions that are occurring on the human beings that they are tethered to.

As a general rule, existing devices are either affixed to the wrist via a wristband, to the upper arm through an armband, to a shoe via a shoe clip, to the ankle via an ankle strap, or simply clipped onto a garment that the person is wearing. Through wearing these sensors, the motion of the person is registered, and can thereafter be subjected to motion analysis regarding the activities of the person. Such units typically detect human motions at the point where they are tethered to the body, and thereafter use those motions as being representative of the entire person.

Human beings have arms, legs, a head and a torso, all of which can have relatively different movements. The movement of a person's wrist is very different from the movement of that person's ankle, which in turn differ markedly from the movement of that person's torso or head. It is important to measure the movement in a region of the body that is most representative of the entire body—invariably that region is the torso.

Motion-sensing devices that are worn by human beings need to be small and desirable to wear. A device that is large and ungainly is unlikely to be worn continuously, or even at all.

For motion sensing that occurs around the clock, the user may be required to remove the device and re-tether it at various times during the day—from sleep to housework to fitness activities to working at the office to traveling outdoors. Removal and re-attachment of the device to the body or a garment can be inconvenient to people. Furthermore, clipping and unclipping the device from one garment to the next (e.g. from sleepwear to workout wear to office wear to evening wear, and back to sleepwear) presents the risk that the person may forget to do it and lose the motion sensor or have it land in the laundry.

Lastly, for the motion sensing to be most effective, it is desirable that it be directly in touch with the torso rather than clipped onto a garment. Unless the garment is worn tightly on the human being, the movement of the garment may not be identical to the movement of the human being. For example, a motion sensor affixed to a shirt pocket will measure the movement of the shirt pocket. If the shirt flops a bit relative to the torso of the person, then that motion sensor may also capture artifacts of the body's motion, not the pure motion of the torso. Another example is that of a necklace where the motion sensor is encased in the pendant of the necklace, hanging from the neck. As the person moves this pendant will have a tendency to swing around while being worn, thereby not capturing accurately the motion of the body.

Figure 1:
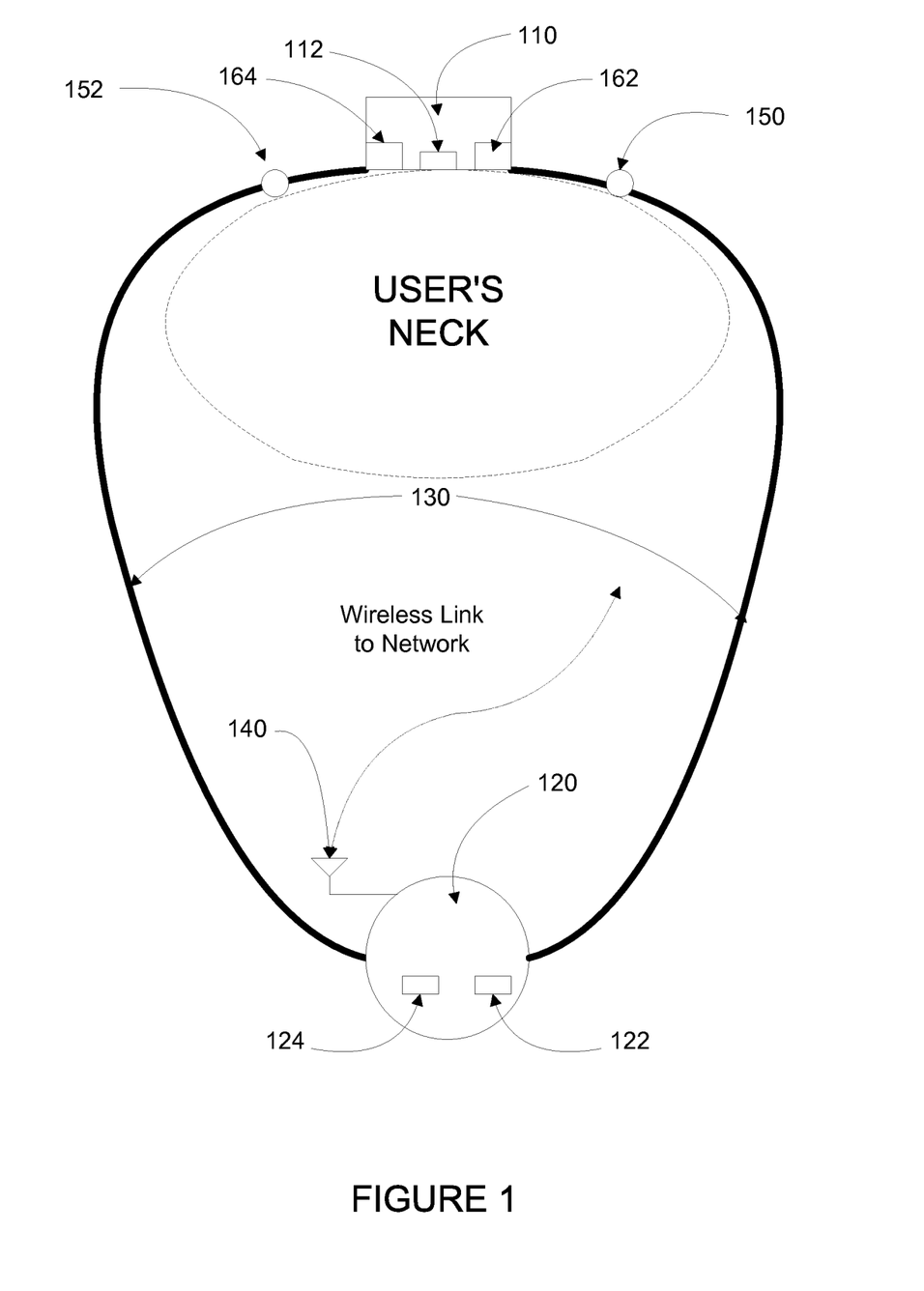
FIG. 1 shows an example of an embodiment of a wearable motion sensing device.

FIG. 1 shows an example of an embodiment of a wearable motion sensing device. This embodiment of the wearable motion sensing device includes a motion sensor 110 and a pendant 120. An insulated conductor 130 provides an electrical connection between the motion sensor 110 and the pendant 120. When worn by, for example, a human being, the motion sensor 110 can sense motion of the human being. Electrical signals that represent the sensed motions can be received by the pendant 120 through, for example, the insulated conductor 130.

The motion sensor 110 can include a motion sensor 112, such as a tri-axial an accelerometer for generating an electrical signal based on motion of the motion sensor. The pendant 120 can include a processor 122 for receiving the electrical signals (at least a representation of the electrical signals) and performing processing to identify the sensed motions. In some cases, communications circuitry 124 of the pendant can be used to communicate the sensed motions to a network. The communications can be wireless, and transmitted and/or received by the pendant through an antenna 140.

Additionally, the pendant can include a battery to power the processor 112 and the communications circuitry 124. Battery power can be provided to the motion sensor 110 through the insulated conductor 130, or the motion sensor 110 can include its own battery.

For an embodiment, the wearable motion sensing device can be worn like a necklace around a user's neck. The pendant 120 can be attached to the wearable motion sensing device at a location of the wearable motion sensing device relative to the motion sensor 110 that when worn by a human being, a mass of the pendant 120 urges the motion sensor 110 towards the human being. More specifically, the motion sensor 110 is urged towards the human being's neck, thereby providing an accurate representation of motion of the human being's torso. For an embodiment, the motion sensor is attached to the necklace at a diametrically opposed location of the necklace as to where the pendant is attached to the necklace.

The described embodiments provide several advantageous features. An embodiment includes a necklace that has two parts. A first part is a clasp which when worn is located right behind the neck of the human wearing the necklace, and is typically in contact with the body. The second part includes the pendant hanging around the front of the neck or the chest. For an embodiment, the motion sensor is embedded in the clasp of the necklace, whereas the pendant contains other electronics that are required for the sensor to operate (these could be the CPU, battery, flash, memory, wireless circuitry, beepers, and other ancillary circuitry). The clasp containing the motion sensor is electrically connected to the pendant via the necklace chain, which contains wires to send electrical signals between the motion sensor and the pendant. These electrical leads are insulated, so that any other metal in the chain or contact with the human skin will not cause any electrical shorting or distortion of the electrical signal. The necklace may be designed to be ornamental, such that people would want to wear it, and there can be various styles of it suitable to women and men.

For embodiments, the clasp of the necklace is tiny and unobtrusive. The clasp is constantly in contact with the skin at the back of the neck. However, it can be acceptable to be behind the collar of a garment. The locket or pendant contains most of the remaining electronics of the motion sensing device, including the battery, CPU, wireless circuitry and more. Although the locket or pendant may swing around as the person is wearing the necklace, the clasp at the back of the neck will essentially be moving in direct concert with the movement of the person's torso, or more specifically the person's neck.

Several characteristics of the necklace lend themselves to accurate detection of motion around the clock. The necklace can essentially be worn continuously, and users (those who wear the necklace) do not need to take it on and off as they transition through their various daily activities. This makes accidental loss of the device less likely, as well as having the device land in an undesirable place such as a laundry basket or the floor. The motion sensor 110 is typically in contact with the human skin, and as such its movements are directly those of the human torso. These movements are unfettered by any relative motions of the person's garments. The necklace motion sensor can be worn during a person's shower, and does not need to be removed when they are in the bathroom. The necklace can be made small and attractive, such that people would want to wear it. Any number of decorative styles is possible to suit different personal preferences.

The wearable motion sensing device can additionally include electrodes 150, 152 which are electrically connected to a conductor within the electrical conductor 130. Electrical signals of the electrodes 150, 152 can be coupled to electrocardiogram processing located, for example, in the pendant 120. The electrodes 150, 152 are preferably located so that when the wearable motion sensing device is worn by a user, the electrodes 150, 152 physically contact the skin of the user, for example, the skin on the back of the user's neck. An embodiment includes the electrodes 150, 152 being collocated with the motion sensor 110. An electrocardiogram (EKG or ECG) is a test that checks for problems with the electrical activity of your heart, and allows for determination of the user's heart rate rhythm. This embodiment provides an alternative to traditional chest wraps.

Additionally, as shown the sensor 110 or clasp can additionally include a temperature sensor 162 and/or a moisture sensor 164. Similar to the electrodes, the temperature sensor 162 and the moisture sensor 164 are preferably in physical contact with the user's skin.

Figure 2:
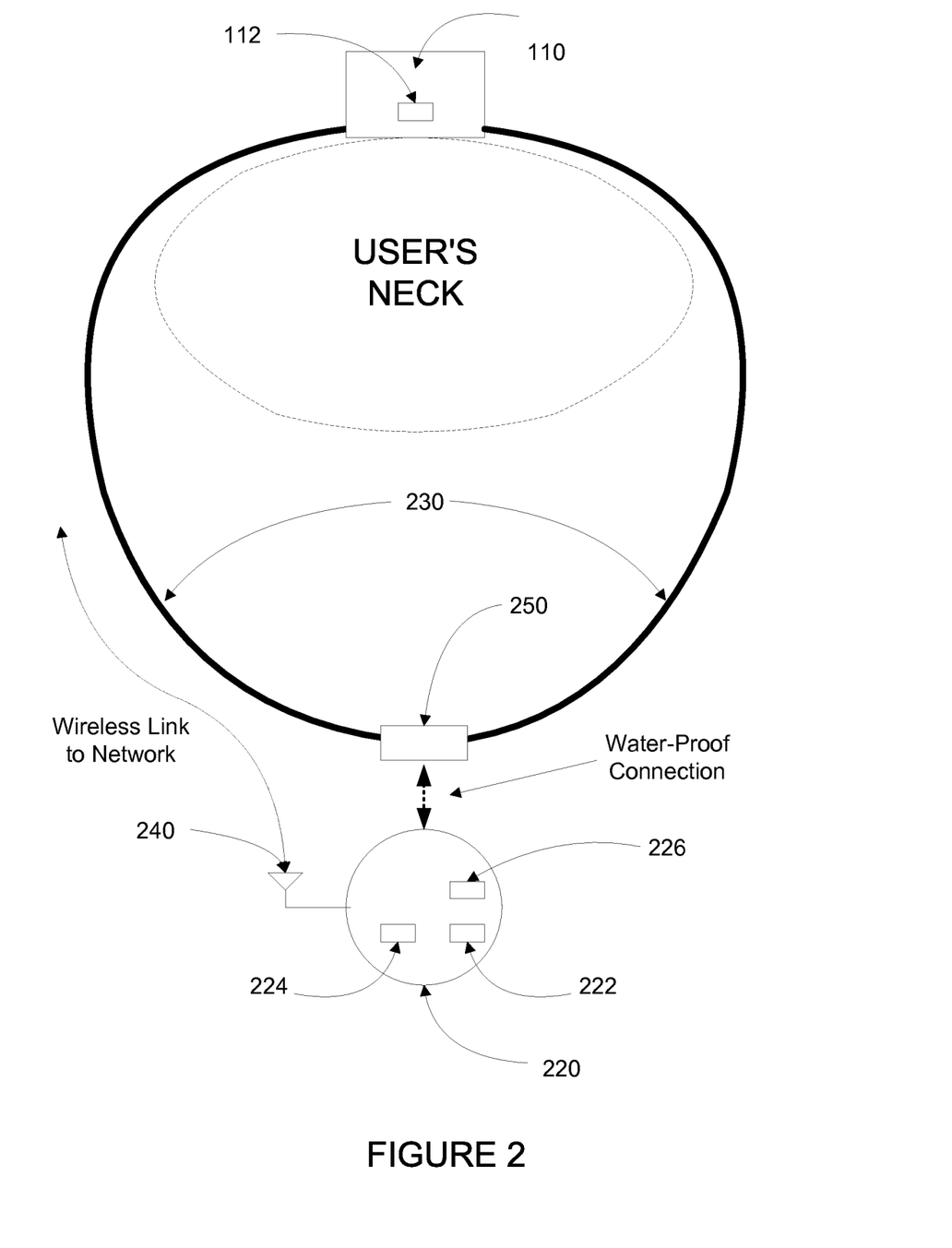
FIG. 2 shows an example of another embodiment of a wearable motion sensing device.

FIG. 2 shows an example of another embodiment of a wearable motion sensing device. As previously described, this embodiment includes a motion sensor 110 that includes, for example, an accelerometer 112.

For this embodiment, however, the pendant 220 can be detached and reattached to the wearable motion sensing device. The wearable motion sensing device includes a point of attachment 250 that allows the pendant 220 to be electrically connected to the motion sensor 110 through the insulated conductor 230 when the pendant 220 is connected or attached to the wearable motion sensing device. It can be desirable for the connection of the pendant 220 to the point of attachment 250 to be water proof so that the user (one who wears the wearable motion sensing device) can, for example, take a shower.

An embodiment of the pendant 220 includes its own motion sensor 226. When the pendant 220 is not attached to the wearable motion sensing device, the pendant can operate completely independently from the wearable motion sensing device. For example, in one mode, the pendant 220 can be clipped to a user's belt. However, when taking a shower, the user may be required to use the wearable motion sensing device and attach the pendant 220 to allow continuous monitoring of the user's motions. As previously described, the pendant 220 can detect whether or not it is attached to the wearable motion sensing device, and operate accordingly.

As previously described, embodiments of the pendant 220 can include a processor 222 for receiving the electrical signals (at least a representation of the electrical signals) and performing processing to identify the sensed motions. In some cases, communications circuitry 224 of the pendant can be used to communicate the sensed motions to a network. The communications can be wireless, and transmitted and/or received by the pendant through an antenna 240.

Figure 3:
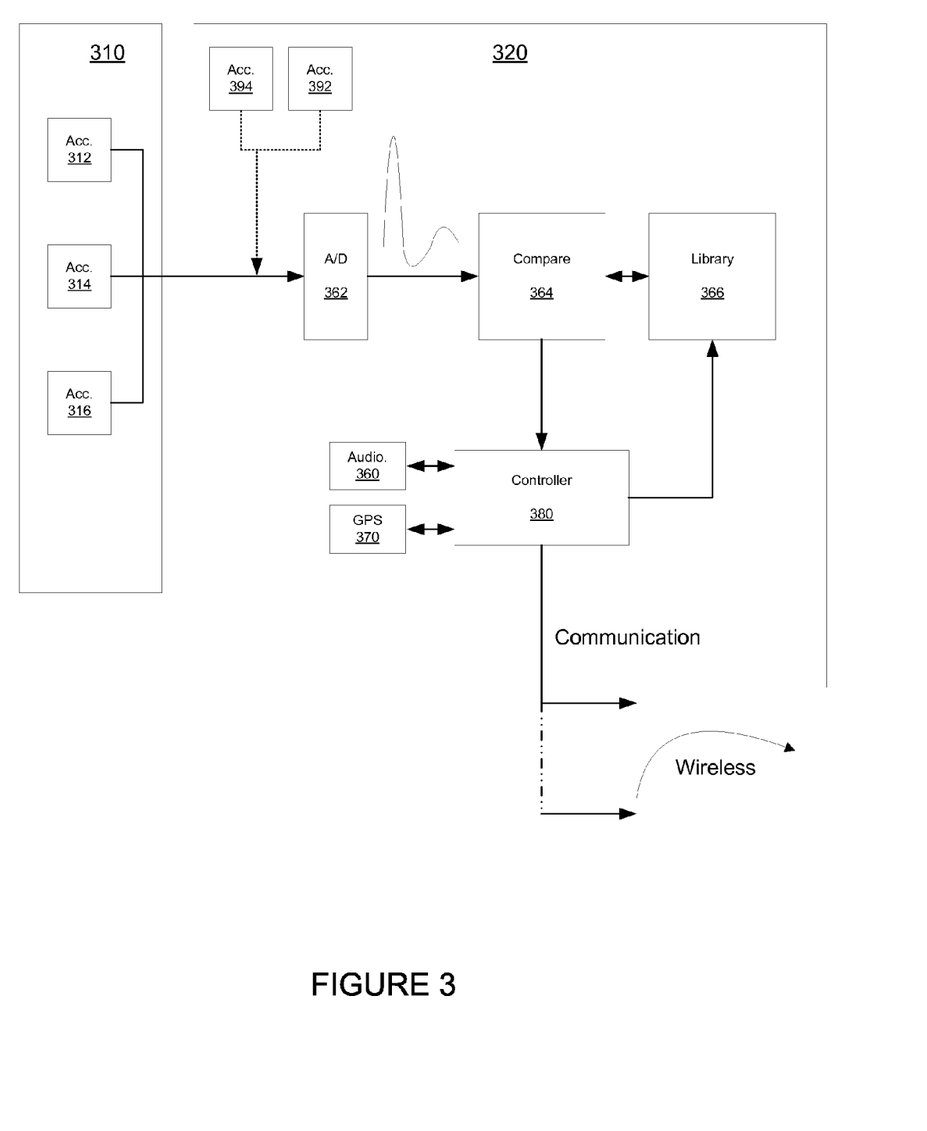
FIG. 3 shows a block diagram of an embodiment of a wearable motion sensing device.

FIG. 3 shows a block diagram of an embodiment of a wearable motion sensing device. The motion sensor 310 can include one or more motion sensors, such as, accelerometers 312, 314, 316. The motion sensor 310 can be electrically connected to the pendant 320 through the previously described insulated conductor 130.

This embodiment of the pendant 320 includes an analog to digital converter (ADC) 362 that digitizes the analog accelerometer signals. The digitized signals are received by compare processing circuitry 364 that compares the digitized accelerometer signals with signatures that have been stored within a library of signatures 366. Each signature corresponds with a type of motion. Therefore, when a match between the digitized accelerometer signals and a signature stored in the library 366, the type of motion experienced by the motion detection device can determined. A controller 380 can manage the signature matching process.

An embodiment includes filtering the accelerometer signals before attempting to match the signatures. Additionally, the matching process can be made simpler by reducing the possible signature matches.

An embodiment includes identifying a previous human activity context. That is, for example, by knowing that the previous human activity was walking, certain signatures can intelligently be eliminated from the possible matches of the present activity that occurs subsequent to the previous human activity (walking).

An embodiment includes additionally reducing the number of possible signature matches by performing a time-domain analysis on the accelerometer signal. The time-domain analysis can be used to identify a transient or steady-state signature of the accelerometer signal. That is, for example, sitting sedentary in a chair may have a prominent steady-state signature, a walk may have a prominent rhythmic signature, whereas a fall may have a prominent transient signature. Identification of the transient or steady-state signature of the accelerometer signal can further reduce or eliminate the number of possible signature matches, and therefore, make the task of matching the accelerometer signature with a signature within the library of signature simpler, and easier to accomplish. More specifically, the required signal processing is simpler, easier, and requires less computing power.

Upon detection of certain types of motion, an audio device 360 and/or a global positioning system (GPS) 370 can engaged to provide additional information that can be used to determine the situation of, for example, a human being the motion detection device is attached to.

The condition, or information relating to the motion detection device can be communicated through a wired or wireless connection. A receiver of the information can process it, and make a determination regarding the status of the human being the motion detection device is attached to.

As additionally shown in FIG. 3, another embodiment of the pendant 320 includes on-board motion sensors (accelerometers 392, 394) that the pendant 320 can utilize when the pendant 320 is disconnected from the wearable motion sensing device. In this mode, the pendant may be attached, for example, to a belt clip of the user.

Figure 4:
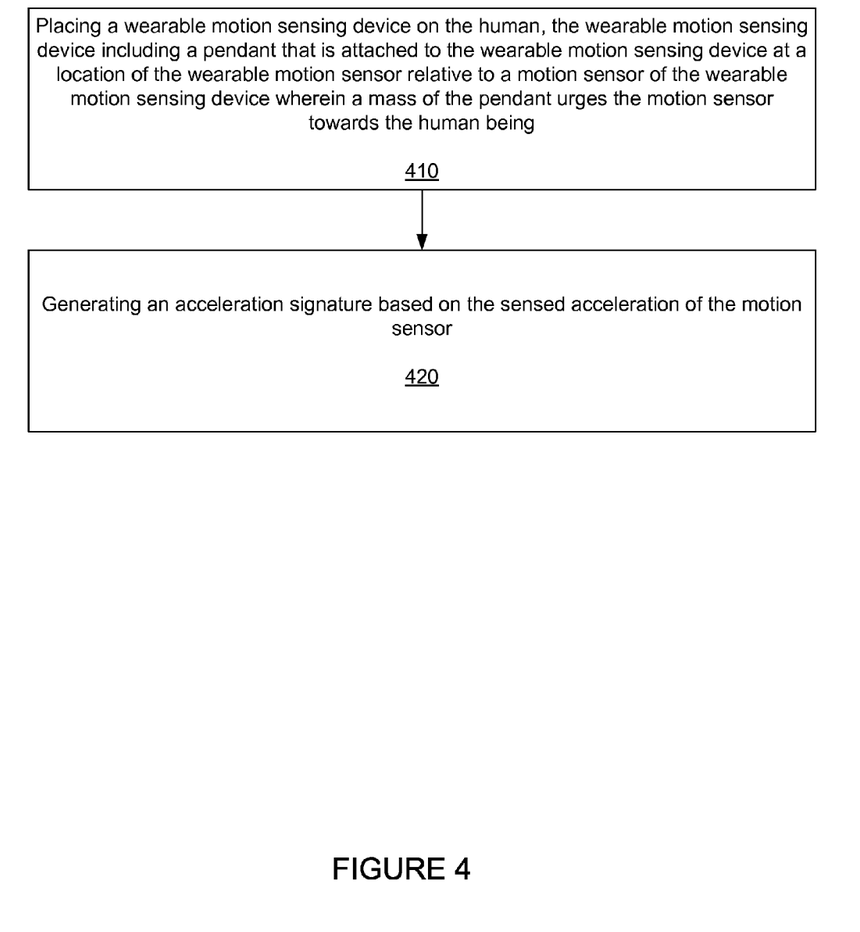
FIG. 4 is a flow chart that includes steps of an example of a method of detecting motion of a human.

FIG. 4 is a flow chart that includes steps of an example of a method of detecting motion of a human. A first step 410 includes placing a wearable motion sensing device on the human, the wearable motion sensing device including a pendant that is attached to the wearable motion sensing device at a location of the wearable motion sensing device relative to a motion sensor of the wearable motion sensing device wherein a mass of the pendant urges the motion sensor towards the human being. A second step 420 includes generating an acceleration signature based on the sensed acceleration of the motion sensor.

As previously described, the acceleration signatures are matched with at least one of a plurality of stored acceleration signatures, wherein each stored acceleration signatures corresponds with type of motion. The type of motion of the object human is identified based on matching of the acceleration signature. For an embodiment, the motion sensor includes accelerometers that detect motion of the motion sensor, and the pendant comprises processing circuitry for matching and identifying the type of motion.

As previously described, an embodiment of the pendant includes at least one accelerometer. Additionally, the pendant detects whether it is attached to the wearable motion sensing device. If the pendant is attached to the wearable motion sensing device, then the pendant receives detected motion signals, matches an identifying motion of the received motion signals. If the pendant is not attached to the wearable motion sensing device, then the pendant generates its own matching motion signals, and identifies its own motion.

An embodiment includes the pendant of the wearable motion sensing device determining what network connections are available to the wearable motion sensing device. The wearable motion sensing device distributes at least some of the acceleration signature matching processing if processing capability is available to the motion detection device though available network connections. For an embodiment, the wearable motion sensing device distributes the acceleration signature matching processing if the processing capability is available to wearable motion sensing device through available network connections, and distributing the acceleration signature matching processing saves the wearable motion sensing device processing power. For an embodiment, the wearable motion sensing device distributes the acceleration signature matching processing if the processing capability is available to the wearable motion sensing device through available network connections, and distributing the acceleration signature matching processing increases a speed of the processing of the wearable motion sensing device.

Figure 5:
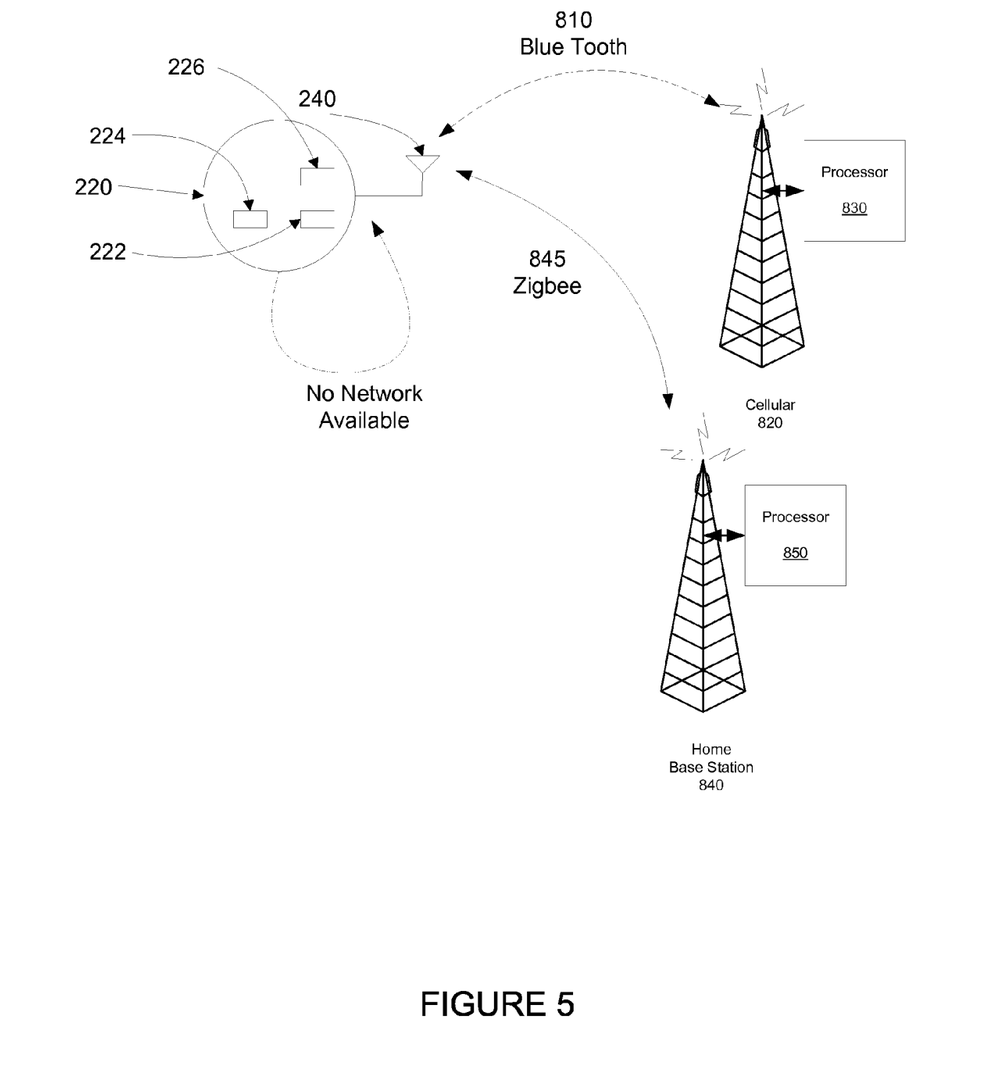
FIG. 5 shows a wearable motion sensing device that can be connected to one of multiple networks.

FIG. 5 shows a wearable motion sensing device that can be connected to one of multiple networks. As shown, the pendant 220 can be connected to one of multiple networks. Examples of possible networks (not a comprehensive list) the pendant 220 can connect to, include a cellular network 820 through, for example, a blue tooth wireless link 810, or to a home base station 840 through, for example, a Zigbee wireless link 845. The wireless links 810, 845 can each provide different levels of bandwidth. Each of the networks includes available processing capabilities 830, 850.

If the pendant 220 does not have any network connections available, the pendant 220 must perform its own matching processing. If this is the case, then the processing algorithms may be less complex to reduce processing power, and/or reduce processing speed. For example, the matching processing can be made simpler by comparing threshold levels for elemental motions by extracting significant wavelet coefficients. Acceleration signals data acquisition is performed in chunk of processing every few milliseconds by waking up. For all other times the processor rests in low-power mode. Except for the emergency situation, the RF communication is done periodically when the data is in steady state, there is no need to send it to network i.e. when the object is in sedentary there is no need to send data change in the state is communicated to network. Additionally, if no network connections are available, the operation of the wearable motion sensing device may be altered. For example, if the wearable motion sensing device detects an emergency situation (such as, a fall), the motion wearable motion sensing device (that is, the pendant 220) may generate an audio alert. If a network connection was available, the audio alert may not be generated, but an alert may be transmitted over the available network.

The pendant 220 includes a processor in which at least a portion of the analysis and signature matching can processing can be completed. However, if the pendant 220 has one or more networks available to the pendant 220, the motion detection device can off-load some of the processing to one of the processors 830, 850 associated with the networks.

The determination of whether to off-load the processing can be based on both the processing capabilities provided by available networks, and the data rates (bandwidth) provided by each of the available networks.

Figure 6:
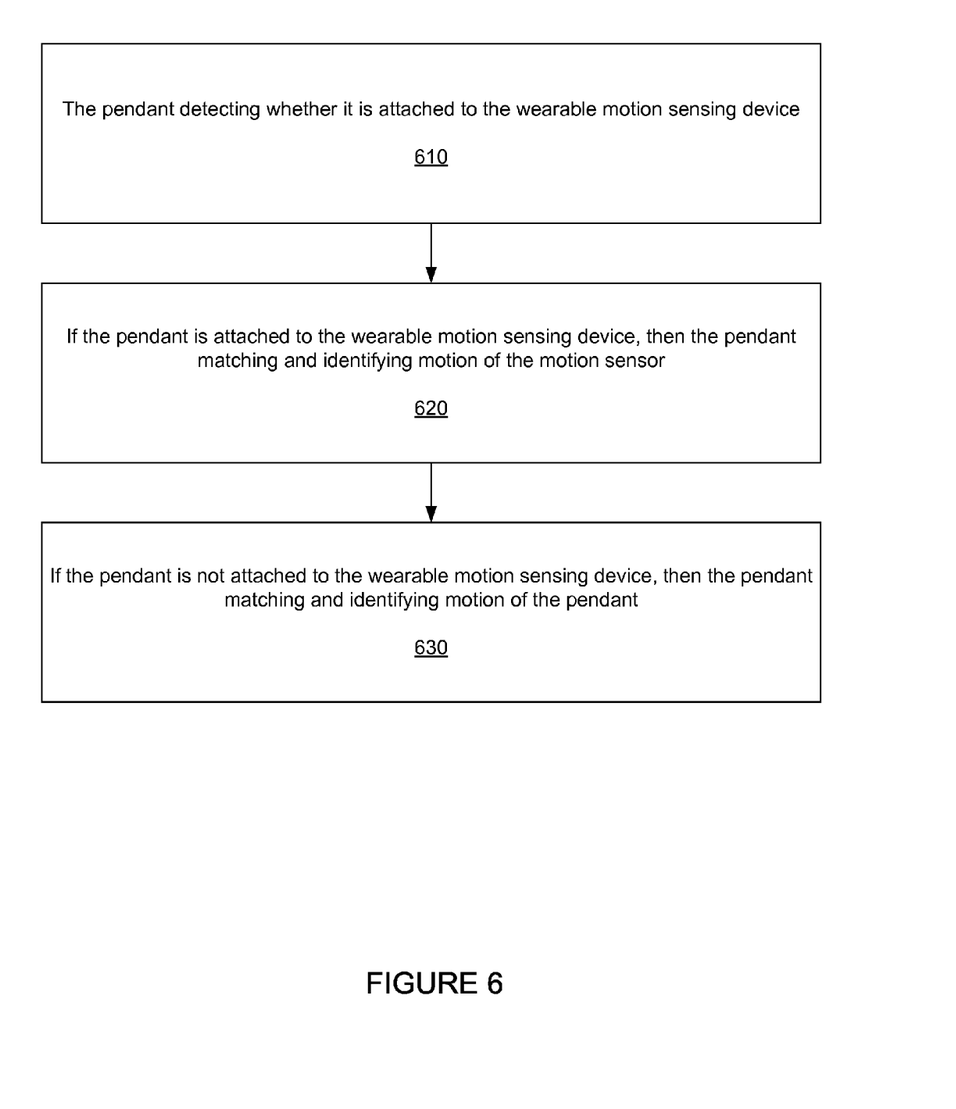
FIG. 6 is a flow chart that includes steps of one example of a method of a pendant detecting whether it is attached to a wearable motion sensing device

FIG. 6 is a flow chart that includes steps of one example of a method of a pendant detecting whether it is attached to a wearable motion sensing device. For this embodiment, the pendant includes at least one accelerometer. A first step 610 includes the pendant detecting whether it is attached to the wearable motion sensing device. A second step 620 includes if the pendant is attached to the wearable motion sensing device, then the pendant matching and identifying motion of the motion sensor. A third step 630 includes if the pendant is not attached to the wearable motion sensing device, then the pendant matching and identifying motion of the pendant.

When pendant is connected to the lanyard (necklace), the controller in the pendant receives a silicon signature response for a specific address over I2C bus from the accelerometer. This signal is the op-code for the protocol over I2C. The controller switches to the accelerometer on the lanyard. It stops processing the signals from the accelerometer on the pendant. When the lanyard connection is removed, the controller on the pendant stops receiving the silicon signature at the expected address. In this scenario, the controller switches to process the signals from the accelerometer on the pendant.

Figure 7:
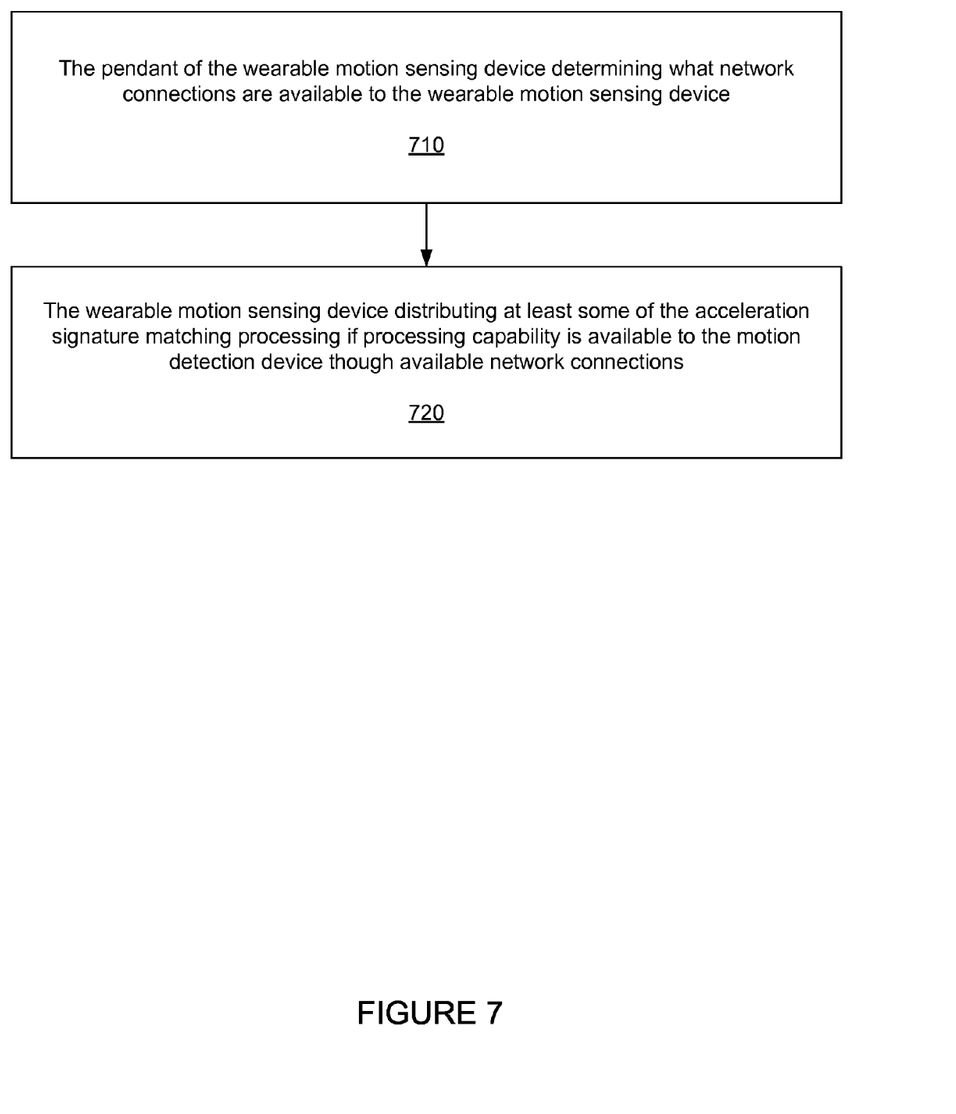
FIG. 7 is a flow chart that includes steps of one example of a method of a wearable motion sensing device checking network availability for improvements in speed and/or processing power of acceleration signature matching.

FIG. 7 is a flow chart that includes steps of one example of a method of a wearable motion sensing device checking network availability for improvements in speed and/or processing power of acceleration signature matching. A first step 710 includes the pendant of the wearable motion sensing device determining what network connections are available to the wearable motion sensing device. A second step 720 includes the wearable motion sensing device distributing at least some of the acceleration signature matching processing if processing capability is available to the motion detection device though available network connections.

As previously described, an embodiment includes the wearable motion sensing device distributing the acceleration signature matching processing if the processing capability is available to wearable motion sensing device through available network connections, and distributing the acceleration signature matching processing saves the wearable motion sensing device processing power. Also as described, an embodiment includes the wearable motion sensing device distributing the acceleration signature matching processing if the processing capability is available to the wearable motion sensing device through available network connections, and distributing the acceleration signature matching processing increases a speed of the processing of the wearable motion sensing device.

Although specific embodiments have been described and illustrated, the embodiments are not to be limited to the specific forms or arrangements of parts so described and illustrated.

What is claimed:

1. A wearable motion sensing device, comprising:
    a necklace,
    a motion sensor attached to the necklace; and
    a pendant attached to the necklace, wherein the motion sensor is attached to the necklace at a diametrically opposed location of the necklace as to where the pendant is attached to the necklace, wherein a mass of the pendant urges the motion sensor towards a back of a neck of the human being when the necklace is worn by the human being;
    wherein the necklace further comprises insulated electrical conductors that electrically connect the motion sensor to the pendant, allowing a power supply of the pendant to provide electrical power to the motion sensor; and
    wherein the pendant is detachable from the necklace and the pendant includes a processor circuit configured to detect whether the pendant is attached to the necklace and;
    if the pendant is detected to be attached to the necklace, then the processor circuit is further configured to identify motion of the motion sensor, and
    if the pendant is detected to be detached from the necklace, then the processor circuit is further configured to identify motion of the pendant.

2. The device of claim 1, wherein the necklace further comprises insulated electrical conductors that electrically connect the motion sensor to the pendant, allowing the processor of the pendant to receive sensed signals of the motion sensor.

3. The device of claim 1, wherein the pendant comprises at least one of a battery, a central processing unit, wireless communications circuitry, an audio beeper, and a microphone.

4. The device of claim 1, wherein the motion sensor senses motion of the human being, and electrical circuitry of the pendant monitors the sensed motion.

5. The device of claim 4, wherein the motion sensor comprises at least one accelerometer for generating an acceleration signature based on the sensed acceleration of the motion sensor, and wherein the pendant comprises:
 means for matching the acceleration signature with at least one of a plurality of stored acceleration signatures, wherein each stored acceleration signatures corresponds with a type of motion; and
 means for identifying the type of on of the motion sensor based on the matching of the acceleration signature.

6. The device of claim 1, wherein the motion sensor further comprises a temperature sensor.

7. The device of claim 1, wherein the motion sensor further comprises a moisture sensor.

8. The de vice of claim 1, further comprising a first electrode and a second electrode, and the pendant further comprising an electrocardiogram processor, the pendant electrocardiogram processor configured to receive an electrical signal from the human being via the first and second electrodes.

9. A method of detecting motion of a human, comprising:
 generating an acceleration signature based on acceleration of a motion sensor that is coupled to a necklace and is configured to be worn at a rear neck area of the human;
 detecting, using a processor circuit in a pendant that is attachable to the necklace, whether the pendant is attached to the motion sensor; and
 when the processor circuit detects that the pendant is attached to the motion sensor, identifying a type of motion of the motion sensor, and
 when the processor circuit detects that the pendant is not attached to the motion sensor, identifying a type of motion of the pendant;
 wherein the motion sensor includes one or more accelerometers that detect motion of the human.

10. A method of detecting motion of a human, comprising:
 placing a wearable motion sensing device on the human, the wearable motion sensing device including a pendant that is attached to the wearable motion sensing device at a location of the wearable motion sensing device relative to a motion sensor of the wearable motion sensing device wherein a mass of the pendant urges the motion sensor towards the human being;
 generating an acceleration signature based on sensed acceleration of the motion sensor; wherein motion sensor includes accelerometers that detects motion of the motion sensor, and the pendant comprises processing circuitry for matching and identifying a type of motion;
 wherein the motion sensor includes accelerometers that detect motion of the motion sensor, and the pendant comprises processing circuitry for matching and identifying a type of motion; and further comprising:
 the pendant detecting whether it is attached to the wearable motion sensing device;
 if the pendant is attached to the wearable motion sensing device, then the pendant matching and identifying motion of the motion sensor; and
 if the pendant is not attached to the wearable motion sensing device, then the pendant matching and identifying motion of the pendant.

11. The method of claim 10, wherein the wearable motion sensing device distributes an acceleration signature matching processing if a processing capability is available to the wearable motion sensing device through available network connections, wherein distributing the acceleration signature matching processing saves the wearable motion sensing device processing power.

12. The method of claim 10, wherein the wearable motion sensing device distributes an acceleration signature matching processing if the processing capability is available to the wearable motion sensing device through available network connections, wherein distributing the acceleration signature matching processing increases a speed of the processing of the wearable motion sensing device.

\* \* \* \* \*